United States Patent [19]

Eyal

[11] Patent Number: 6,022,992
[45] Date of Patent: Feb. 8, 2000

[54] ACID-SALT METATHETIC PROCESS

[75] Inventor: Aharon Eyal, Kibbutz Ramat Rachel, Israel

[73] Assignee: Yissum Research Development Company of the Hebrew University of Jerusalem, Jerusalem, Israel

[21] Appl. No.: 09/043,419

[22] PCT Filed: Sep. 9, 1996

[86] PCT No.: PCT/IL96/00105

§ 371 Date: May 28, 1998

§ 102(e) Date: May 28, 1998

[87] PCT Pub. No.: WO97/11047

PCT Pub. Date: Mar. 27, 1997

[30] Foreign Application Priority Data

Sep. 19, 1995 [IL] Israel ......................................... 115346

[51] Int. Cl.[7] .......................... C07C 59/265; C07C 59/08
[52] U.S. Cl. .......................... 562/589; 423/181; 423/395; 423/399; 562/513; 562/575; 562/584; 562/589
[58] Field of Search ..................................... 423/181, 395, 423/399; 562/513, 575, 584, 589

[56] References Cited

U.S. PATENT DOCUMENTS

| 3,944,606 | 3/1976 | Rieger | 260/535 P |
|---|---|---|---|
| 4,275,234 | 6/1981 | Baniel | 562/584 |
| 4,291,007 | 9/1981 | Baniel | 423/390 |
| 4,818,409 | 4/1989 | Puetter | 210/638 |

FOREIGN PATENT DOCUMENTS

| 0017500 | 10/1980 | European Pat. Off. . |
|---|---|---|
| 0517242 | 12/1992 | European Pat. Off. . |

OTHER PUBLICATIONS

Korngold, E., et al., "Water Desalination by Ion–Exchange Hollow Fibers," *Desalination* 84:123–135 (1991).

*Primary Examiner*—Peter O'Sullivan
*Attorney, Agent, or Firm*—Browdy and Neimark

[57] ABSTRACT

A cation exchange membrane mediated acid-salt metathetic process. An aqueous salt solution is placed into a first compartment on one side of the membrane together with an organic amine extractant of limited water miscibility, and an aqueous acid solution is placed into a second compartment on the other side of the membrane. Product acid forms in the first compartment and collects in the organic amine extractant from where it is recovered. The process is particularly suitable for the recovery of a carboxylic acid from its salt.

9 Claims, No Drawings

ACID-SALT METATHETIC PROCESS

FIELD OF THE INVENTION

The present invention is in the field of acid-salt metathetic processes in aqueous solution of the kind that are described by the equation I $$MX + HY \rightleftharpoons MY + HX \qquad \text{I}$$

wherein M stands for a metal cation, H for a proton and X and Y for two different anions.

In the above equation I, the left hand side members MX and HY conventionally denote the starting materials, i.e. the reactants, and the right hand side members MY and HX the products. In keeping with that convention, when the reaction proceeds from left to right it is referred to as a forward reaction and when it proceeds from right to left it is referred to as a backward reaction.

BACKGROUND OF THE INVENTION

Metathetic processes of the kind specified occur in aqueous solution under conditions in which the forward reaction is favored. Where one of the products MY and HX is water insoluble or volatile and accordingly precipitates or evaporates from the solution, the equilibrium of the reaction is constantly shifted from left to right leading to a continuous forward reaction. Depending on whether the desired product is the salt MY or the acid HX or possibly the two of them, the reaction solution and/or the precipitate must be worked up for the recovery of the desired product therefrom. Where, however, both the product MY and HX are water soluble, a steady state will be reached after a while in which the forward and backward reactions are in equilibrium and some kind of intervention is accordingly required for inducing continuation of the forward reaction. In the following, a metathetic reaction of the kind specified in which one of the two products is of limited water solubility or higher volatility and accordingly separates from the aqueous reaction mixture in the course of the reaction, will be referred to as spontaneous forward reaction while a reaction in which both products are water soluble and intervention is required for shifting the equilibrium from left to right and thereby induce continuation of the forward reaction, will be referred to as an induced forward reaction.

A typical example of metathetic processes with spontaneous forward reactions are the so-called wet process production of phosphoric acid by reaction of calcium phosphate with sulfuric acid, and the recovery of citric acid from a fermentation liquor by the so-called liming/acidulation process, which may be described, respectively, by the following Equations II and III $$Ca_3(PO_4)_2 + 3H_2SO_4 = 3CaSO_4 + 2H_3PO_4 \qquad \text{II}$$

$$Ca_3(Cit)_2 + 3H_2SO_4 = 3CaSO_4 + 2H_3PO_4 \qquad \text{III}$$

Typical examples for metathetic processes with induced forward reactions are production of the multi-nutrient fertilizer potassium nitrate from potassium chloride and nitric acid, in which the product of interest is a salt; and the conversion of ammonium lactate, which is a direct product of lactic acid fermentation, into free lactic acid by reaction with sulfuric acid, the product of interest here being an acid. These two processes are described, respectively, by the following equations IV and V $$KCl + HNO_3 = KNO_3 + HCl \qquad \text{IV}$$

$$2NH_4La + H_2SO_4 = (NH_4)_2SO_4 + 2HLa \qquad \text{V}$$

where La is lactate.

In reaction IV the main product is $KNO_3$ and in reaction V the product of interest is HLa. In both reactions, the products are water soluble which makes it necessary to induce the forward reaction.

Solvent extraction is commonly applied for the inducement of forward reactions by product separation in metathetic processes. Alkanols, ethers, esters, ketones and other oxygen-carrying, water-immiscible compounds are well known acid extractants operating through salvation of the acid (solvating extractants). Acid binding in such extracting operations is relatively weak and as a result, the solvating extractants are effective only at relatively high acid activities, and by themselves are, as a rule, not capable of providing the driving force required for the inducement of the forward reaction. While the reaction of potassium chloride with sulfuric acid to form potassium sulfate and hydrochloride acid can be facilitated by acid extraction with alkanols, at the acidity levels required for efficient extraction, the acidic salt $KHSO_4$ is formed rather than $K_2SO_4$. In addition, $Cl^-/SO_4^{2-}$ extraction selectively is low which entails that for effective separation of HCl from $KHSO_4$ many extraction stages are required. Quite generally, due to low binding energy, solvating extractants are not effective for inducement of the displacement of a strong acid by a weak one.

Amine based extractants are much stronger acid binders and thus effective also at low acidities. They are accordingly capable of providing acids, the driving force for metathetic processes in which weak acids react with salts of strong acids, and they are accordingly widely used for the withdrawal of product acids and the inducement of the forward reaction in a metathetic process.

Amine based extractants have, as a rule, a high anion/anion selectivity and thus provide for good separation from each other of the anions in the system and thereby for higher yields and higher purities of the products. This high selectivity may, however, become counter productive and induce backward reactions in cases where the starting acid HY is preferentially extracted and this indeed is the case in the process according to equation IV above in that from a solution containing the ions $Cl^-$, $NO_3^-$, $H^+$ and $K^+$, $HNO_3$ is extracted preferentially by amine based extractants and it is for this reason that amine based extractants cannot be used in the case of equation IV and less attractive solvent extractants or other means are required. Thus, in industrial processes for $KNO_3$ production, the by-product HCl is removed through chemical conversion. In one process KCl and $HNO_3$ are reacted at temperature, concentration and acidity at which oxidation/reduction reactions take place whereby chlorine, nitrogen oxides and other products are formed. Complex separations procedures, NOx conversion to nitric acid and operation at highly corrosive conditions, all of which are required for inducing the forward reaction, result in low profitability.

$KNO_3$ production from KCl and $NHO_3$ can also be mediated by ion exchangers. Passage of a KCl solution through a cation exchanger in its acid form results in loading the resin with $K^+$ ions and formation of an HCl solution. The cation exchanger is then eluted with an $HNO_3$ solution to produce $KNO_3$ and regenerate the cation exchanger. Alternatively, it is possible to transfer KCl solution through $NO_3^-$ loaded anion exchanger which is then regenerated by $HNO_3$.

Likewise, solvent extraction with an amine based extractant also induces backward reaction in case of equation V above in that, from an aqueous solution containing $La^-$, $SO_4^-$, $HSO_4^-$, $H^+$ and $NH_4^+$, $HSO_4$ is extracted preferentially whereby the backward reaction is induced. Solvating extractants have the required selectivity and extract lactic acid from the solution without, however, yielding the advantages afforded by amine based extractants. Accordingly, it has been proposed to recover lactic acid from a fermentation broth by processes other than a metathetic reaction. Thus, EP 0517242 (Mantovani et al.) describes a process by which the lactate values of a nearly neutral lactic acid fermentation liquor are first separated by means of a carbonate loaded anion exchanger, which is then eluted by ammonium carbonate to form an aqueous ammonium lactate and an ammonium carbonate solution. The ammonium carbonate in solution is decomposed thermally and the ammonium lactate is passed through a cation exchanger in its acid form to yield a lactic acid solution and an ammonium loaded cation exchanger, which latter is regenerated by a mineral acid solution such as aqueous HCl. This process thus involves two ion exchange operations, the first of which provides for purification while the second mediates the metathetic reaction of equation VI

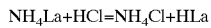

$$NH_4La+HCl=NH_4Cl+HLa \qquad\qquad VI$$

In order to avoid product or by-product contamination and low yield, large volumes of ion exchanger and marked dilution are applied in both the above ion exchange operation. Further dilution is imposed by unavoidable washing of the ion exchanger resin after each stage, all of which results in a dilute product solution. It is thus evident that these and similar processes are cumbersome and not practical for industrial application.

It is the object of the present invention to provide in an acid-salt metathetic process, a new method for inducing forward reactions.

SUMMARY OF THE INVENTION

The invention makes use of a known technique by which metathetic acid-salt reactions are performed indirectly with cation exchange mediation. Thus Korngold and Vofsi describe in "*Desalination*, 84, 123 (1991) a process for the removal of salts from water, comprising in a first stage interaction of a salt contained in a first aqueous solution within a first compartment with an acid contained in a second aqueous solution within a second compartment, which compartments are separated from each other by a cation exchanger membrane. In the course of the process the cation of the salt transfers via the membrane from the first to the second solution and protons are transferred in the opposite direction to the first compartment. As a result, an acid is formed in the salt compartment and a salt in the acid compartment.

U.S. Pat. No. 4,818,409 (Puetter et al.) describes a process for obtaining an aqueous solution of a water-soluble organic acid. In accordance with that disclosure, an aqueous solution of a salt of a water-soluble organic acid having a $pK_a$ value>2 is passed through a first compartment on one side of a cation exchanger membrane and an aqueous solution of a mineral acid is passed through a second compartment on the other side of the membrane.

In both these processes, the driving force for the indirect reaction is provided by the reactants themselves without any extraneous inducement. Thus, in the Korngold and Vofsi process the driving force for the indirect reaction and thus the prerequisite for its occurrence, is a high proton concentration, i.e. a high acidity. This prerequisite is, for example, not met in the recovery of an organic acid from a starting solution of its salt, e.g. the recovery of lactic acid from an ammonium lactate broth obtained by lactic acid fermentation processes, where it is preferred to use weak acids. In the Puetter et al. process, the driving force is the high basicity of the organic acid anion and for driving the reaction to completion a strong mineral acid is again required and a relatively weak acid such as, for example, acetic acid or phosphoric acid will in many cases not be effective. The unsuitability of phosphoric acid presents a serious drawback since phosphate salts which can be used as fertilizers, are preferred by-products of carboxylic acid production.

In accordance with the invention it has surprisingly been found that a combination of cation exchanger membrane mediation with solvent extraction of product acid by means of an organic amine extractant, is very effective for the inducement of forward reactions in acid-salt metathetic reactions. It has further been found that as a result of said combination any undesired and counter-productive anion/anion extraction selectivity is avoided.

The invention thus provides in a cation exchanger membrane mediated acid-salt metathetic process in which the starting materials and products are water-soluble and in which an aqueous solution of a starting salt is charged into a first compartment on one side of the cation exchanger membrane and an aqueous solution of a starting acid is charged into a second compartment on the other side of the membrane, the improvement by which the said first compartment is further charged with an organic amine based extractant of limited water miscibility whereby a binary liquid system is formed in said first compartment comprising aqueous and organic phases, and the organic phase is separately withdrawn from said first compartment after a desired residence time for the recovery of a product acid therefrom.

Thus, as distinct from the prior art where the reaction between the starting salt MX and the starting acid HY is direct, in accordance with the invention, it is indirect in being mediated by the cation exchanger membrane with the driving force being provided by the amine based extractant.

The process according to the invention may be carried out batch-wise or continuously. In accordance with one embodiment of a continuous mode of operation, a multi-cell battery is used with alternating first and second compartments, said aqueous solution of a starting salt and said organic amine based extractant being continuously passed through all said first compartments and said aqueous solution of a starting acid being continuously passed through all said second compartments.

In accordance with another embodiment of the continuous mode, there is used a system of hollow fibrous cation exchanger membranes contained within a suitable vessel. The aqueous solution of a starting salt and the amine based extractant are mixed in the vessel while said aqueous solution of a starting acid is flown through the hollow fibrous membranes.

In the performance of the process according to the invention, the cations of the starting salt are transferred from a first to a second compartment, protons are transferred from a second to a first compartment, the product acid is continuously withdrawn into said organic amine extractant of limited water miscibility within a first compartment and in this way there is induced the forward reaction in the cation exchanger membrane mediated acid-salt metathetic reaction. As mentioned, in this process the amine extractant provides the driving force for the performance of the metathetic reaction and makes possible the occurrence of reactions which otherwise would not have been feasible, e.g. reactions between salts and weak acids such as carbonic acid, phosphoric acid, acetic acid and the like. Moreover, unlike in the case of direct reaction in which the anion selectivity of an amine extractant may be counter productive and favor the backward reaction, in the presence of a cation exchanger membrane as taught by the present invention, by which the reaction is rendered indirect, any anion selectivity of the organic amine extractant is of no consequence and does not influence the direction of the reaction.

The use of an organic amine extractant also provides for purification of the product acid from impurities present in the aqueous solution of the starting salt. For example, when applying the invention to the recovery of lactic acid from a nearly neutral fermentation liquor the product lactic acid recovered from the separately withdrawn organic phase, is practically free of hydrophilic neutral impurities.

In the implementation of the process according to the invention, product acid is recovered from the organic phase that is separately withdrawn from a first compartment, and the regenerated organic amine extractant is recycled.

If desired, a product salt may be recovered from the aqueous solution withdrawn from a second compartment, either as a useful by-product where the acid recovered from the organic phase withdrawn from a first compartment is the main product, or as the main product of the process.

Organic amines suitable for use as constituents of extractants are primary, secondary and tertiary amines having a total of at least 18 carbon atoms, and they may be used by themselves or optionally together with diluents such as non-polar hydrocarbons, and/or together with polar or protic extraction enhancers and/or together with water-immiscible organic acids.

Recovery of the product acid from the organic phase withdrawn from a first compartment can be effected by conventional means. Thus, where the product acid is volatile such as in the case of hydrochloric or acetic acid, and the various extractant components have a sufficiently high boiling point and do not form azeotropes with the product acid, the acid can be recovered by distillation.

In case the product acid in the process according to the invention is not volatile and notably in case of non-volatile mineral acids, the organic amine of the extractant is preferably a so-called reversible amine, i.e. an amine which readily releases its acid content into water, and the product acid is withdrawn from the organic phase by back-extraction with water. The so-called reversible amines are relatively weak amines such as, for example, tris-2-ethylhexyl amine, and various aniline derivatives. Another family of suitable extractants are various long-chain organic amines in combination with an organic acid and a hydrocarbon diluent, as described in U.S. Pat. No. 4,291,007.

Also carboxylic acids obtained as products can be recovered from the organic amine extract withdrawn from a first compartment by back-extraction with water. It is, for example, possible to employ the method disclosed in U.S. Pat. No. 4,275,234 according to which back-extraction of the amine extract with water is effected at a temperature higher than the temperature at which the acid is extracted into the extractant, i.e. the temperature of the metathetic reaction. Back-extraction can be further enhanced by adding extractant suppressors such as non-polar diluents to the acid-loaded organic phase (extract) prior to back-extraction and/or by removing from the extract prior to back-extraction enhancers such as alkanols.

Conventional, commercially available cation exchanger membranes such as NEOSEPTA™, SELEMION™ and NAFION™ are suitable for the purposes of the present invention. Typical cation exchanger membranes carry sulfonic groups, such as sulfonated polystyrene interpolymers with neutral polymers; sulfochlorinated polyethylene; sulfonated polysulfone, sulfonic perfluorinated polyolefins; etc.

The invention is highly suitable for metathetic processes in various fields of chemical and biochemical technologies such as recycling of fermentation products, fertilizer production and waste treatment, as shown by the following.

Introduction of an amine based extractant and an aqueous KCl solution on one hand and an aqueous $HNO_3$ solution on the other to a battery of alternating first and second compartments separated by cation exchanger membranes, results in the formation of an HCl loaded extractant in the first compartments and an aqueous $KNO_3$ solution in the second compartments. Similarly, aqueous ammonium lactate and amine based extractant in first compartments and phosphoric, sulfuric or nitric acid in second compartments results in lactic acid loaded extractant and in an aqueous solution of an ammonium salt suitable for use as fertilizer. Fluorosilic acid obtained as a by-product in wet-process phosphoric acid is an attractive source of fluoride for HF production. Reaction with ammonia to form ammonium fluoride and silicic acid is a straightforward reaction but recovery of HF values from ammonium fluoride solutions by known processes was found too complicated to be economic. The current invention provides for an economic recovery through conversion of $NH_4F$ into HF and an ammonium salt such as phosphate, sulfate or nitrate. Another example of application is the conversion of $ZnCl_2$ obtained in waste streams of metal surface treatment, into $ZnSO_4$ which latter is suitable for Zn production through electrowinning.

Solvent extraction is highly suitable for recovery of acids from solutions comprising acids and their salts. Thus, pure phosphoric acid can be recovered from agriculture grade phosphoric acid through extraction by reversible extractants. However, due to presence of cations in the solution (namely $Fe^{+3}$, $Al^{+3}$ and $Mg^{+2}$), up to one third of the phosphate values are not taken up by the extractant and remain in the raffinate as monophosphate. According to the invention, the cation containing acid or the extraction raffinate is fed to first compartments together with an amine-based extractant, and a low-cost acid (HCl, $H_2SO_4$) is fed to second compartments of a battery of alternating compartments separated by cation exchanges membranes, whereby practically all residual phosphate values are recovered.

Acid containing wastes are obtained in many industries such as hydrometallurgic processes and surface treatments. Recovery of acid values through solvent extraction reduce waste treatment costs as compared to neutralization, but does not eliminate waste management as in most cases the remaining salt solution cannot be disposed of. The invention provides for the recovery of the acid values combined with conversion of a waste salt to another one, which is more suitable for further treatment. Thus the acidic waste stream of $TiO_2$ pigment production, containing $H_2SO_4$ and $FeSO_4$, can be treated for the recovery of most of the sulfate values and for conversion of the $FeSO_4$ to $FeCl_2$.

An important application of the present invention is in the field of citric acid recovery from fermentation liquors. The traditional liming/acidulation process has many drawbacks.

Solvent extraction processes, applying amine based extractant, such as described in U.S. Pat. Nos. 3,944,606 and 4,275,234 have the serious limitation of recovering only free acid values and are therefore impractical for the recovery of citric acid from broths obtained by fermentation processes based on molasses as sole carbohydrate source or as an additive to pure carbohydrate. Such nutrients yield, among others, citrate salts as primary fermentation products, which do not report to the extractant. Application of the invention provides for extraction of practically all citric acid values from cation containing fermentation liquors and from other contaminated citric acid streams, with no formation of gypsum as an added benefit.

Hydrophilic neutral impurities present in the reagent salt solution in a first compartment will not follow the cation to the product salt in a second compartment across the cation exchanger membrane, and at the same time the selectivity of the amine based extractant provides for the extraction of the product acid in a pure form. As a result, hydrophilic neutral impurities will not report to either of the products and will remain in the aqueous solution left behind in a first compartment after separate withdrawal of the extractant. In this way, product acids and salts are obtained in pure form which is of particular importance when one of the products is a carboxylic acid recovered from a fermentation broth.

Acid extraction into the organic extractant in the first compartment and salt formation in the second compartment deplete the feed salt solution of ions. Accordingly, osmotic pressure will drive water from the first into the second compartment which enhances the extraction of the acid in the first compartment.

Where the product salt is the product of interest the selection of the starting acid is governed by the nature of the salt to be formed and disposal of the by-product acid should be taken into consideration. Typical examples of starting acids used in accordance with the invention are sulfuric, nitric and hydrochloric acid. $CO_2$ and $SO_2$ may also be used as acid sources. A solution comprising an acid and a salt, e.g. the product of cation exchanger regeneration is also suitable as a reagent acid solution. This aspect is of considerable practical importance since it makes possible to use excess acid for the regeneration of a cation exchanger and use the regeneration effluent liquor to advantage.

Where the product acid is the product of interest, the selection of reagent salts will be governed by economic production considerations. Product acids in the processes according to the invention include amino acids and for their production amino acid salts may serve as reagent salts.

For better understanding the invention will now be illustrated by the following examples to which it is not limited.

EXAMPLE 1

An apparatus was used holding two 30 ml. compartments separated by a Neosepta CN–1™ (Tokoyama Soda) cation exchanger membrane with an active area of 2 cm². The membrane was supplied within an NaCl solution and was therefore rinsed with water prior to its mounting in the apparatus.

The first cell of the apparatus was loaded with 20 gr. of an aqueous 1 mol/kg KCl solution and 5 gr of an organic extractant comprising 1.075 mol/kg of trilaurylamine (Alanine 304™, Henkel), 5% by weight of octanol and kerosene as diluent. The second compartment was loaded with 20 gr of an aqueous solution containing 1 mol/kg of $HNO_3$. The apparatus was kept in a mechanical shaker for 3 days following which the organic phase was separately withdrawn from the first compartment and analyzed by separate proton and chloride determination which showed that it contained 0.38 mol/kg of HCl and practically no $HNO_3$. Analysis of the second compartment showed that it contained 1.9 mmol of $KNO_3$. The withdrawn extractant was regenerated by contact with a solution of ammonia whereby HCl was removed.

In a comparative experiment 5 gr of extractant of the same composition was equilibrated in direct contact in a separatory funnel with an aqueous solution containing 1 mol/kg KCl and 1 mol/kg $HNO_3$. Most of the acid found in the organic phase was $HNO_3$.

EXAMPLE 2

The same apparatus and extractant were used as in Example 1. The aqueous starting salt solution introduced into the first compartment contained 1 mol/kg monosodium citrate and the aqueous starting acid solution introduced into the second compartment contained 1 mol/kg HCl. After 3 days in a mechanical shaker the extractant contained 0.7 mol/kg citric acid with only traces of HCl. The extractant phase was back-extracted by 5 successive equilibrations at 80° C. with water at an organic-to-aqueous ratio of 1:1. Analysis of the combined aqueous solutions show that practically all the citric acid was back-extracted.

In a comparative experiment an extractant of the same composition as above was introduced into the first compartment of the apparatus and an aqueous solution containing monosodium citrate and hydrochloric acid in a concentration of 1 mol/kg each were introduced in to t he second compartment. After 3 days of shaking the extractant remained was nearly free of acid.

EXAMPLE 3

The equipment, extractant and procedure were similar as in the previous examples. The aqueous starting, salt solution contained 1 mol/kg sodium lactate and the aqueous starting acid solution contained 1 mol/kg acetic acid. After 3 days the extractant was loaded with 0.25 mol/kg of lactic acid which was recovered by back-extraction with water at 80° C.

In a comparative experiment 5 gr of extractant and 20 gr of an aqueous solution containing 1 mol/kg of sodium lactate and 1 mol/kg of acetic acid were contacted in a separatory funnel. Exctractant loading, with lactic acid in equilibrium was 0.04 mol/kg.

In another comparative experiment the above extractant and water were introduced into the first compartment of the apparatus and an aqueous solution containing 1 mol/kg of acetic acid into the second compartment. Acid concentration in the extractant after 3 days of shaking was less than 0.04 mol/kg.

I claim:

1. In a cation exchanger membrane mediated acid-salt metathetic process in which the reactants and products are water-soluble and in which an aqueous solution of a starting salt is charged into a first compartment on one side of the cation exchanger membrane and an aqueous solution of a starting acid is charged into a second compartment on the other side of the membrane, the improvement by which the said first compartment is further charged with an organic amine extractant of limited water miscibility whereby a binary liquid system is formed in said first compartment comprising aqueous and organic phases, and the organic phase is separately withdrawn from said first compartment after a desired residence time for the recovery of a product acid therefrom.

2. The process of claim 1 carried out batch-wise.

3. The process of claim 1 carried out continuously.

4. The process of claim 3, carried out in a multi-cell battery with alternating first and second compartments, said aqueous solution of a starting salt and said organic amine extractant being continuously passed through all first compartments and said aqueous solution of a starting acid being continuously passed through said second compartments.

5. The process of claim 3, wherein there is used a system of hollow fibrous cation exchanger membranes contained within a suitable vessel, said aqueous solution of a starting salt and said amine based extractant being mixed in the vessel and said aqueous solution of a starting acid being flown through the hollow fibrous membranes.

6. The process of claim 1, serving for the conversion of a carboxylic acid salt into free carboxylic acid.

7. The process of claim 6, serving for the recovery of lactic acid from a fermentation broth.

8. The process of claim 6, serving for the recovery of citric acid from a fermentation broth.

9. The process of claim 6, serving for the conversion of an amino acid salt into free amino acid.

* * * * *